United States Patent [19]

Falciani et al.

[11] 4,393,205
[45] Jul. 12, 1983

[54] CEPHAPIRINE ESTERS AND SALTS THEREOF

[75] Inventors: Marco Falciani; Renato Broggi, both of Milan, Italy

[73] Assignee: Dobfar S.p.A., Milan, Italy

[21] Appl. No.: 240,945

[22] Filed: Mar. 5, 1981

[30] Foreign Application Priority Data

Mar. 14, 1980 [IT] Italy .............................. 20666 A/80

[51] Int. Cl.³ .......................................... C07D 501/34
[52] U.S. Cl. .......................................... 544/28; 544/23
[58] Field of Search ..................................... 544/23, 28

[56] References Cited

U.S. PATENT DOCUMENTS 3,422,100 1/1969 Crast ...................................... 544/28
3,578,661 5/1971 Havtranek et al. ................... 544/28
4,036,829 7/1977 Ferres et al. .......................... 544/23

Primary Examiner—Paul M. Coughlan, Jr.
Attorney, Agent, or Firm—Oblon, Fisher, Spivak, McClelland & Maier

[57] ABSTRACT

Cephapirine esters having the formula

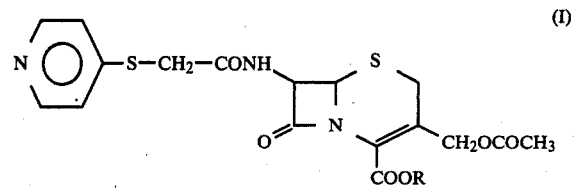

wherein R is selected from the group consisting of

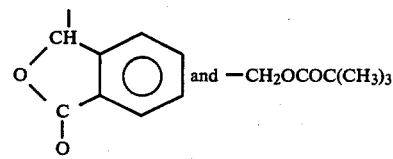 and $-CH_2OCOC(CH_3)_3$ Such esters and salts thereof, having antibiotic activity, are prepared by reacting 7-ACA with bromophtalide or chloromethylpivalate in the presence of an alkylamine, at a temperature in the range of 0°–70° C. The reaction compound is reacted with chlorhydrate chloride of 4-piridylthioacetic acid. A salt of the compound of formula (I) is isolated from the reaction mixture, after washing with acidic water and addition of a pharmaceutically acceptable acid, by treatment with a suitable solvent.

3 Claims, No Drawings

CEPHAPIRINE ESTERS AND SALTS THEREOF

This invention relates to novel cephapirine esters, salts thereof and processes for producing the same. Such esters have the following structural formula

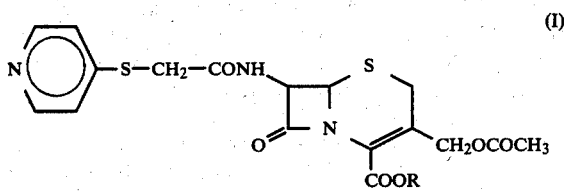

wherein R is selected from the group consisting of:

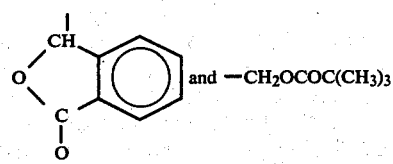

The invention is also concerned with the pharmaceutically acceptable salts of the esters of formula (I), and particularly chorohydrates, paratoluensulphonates and β-naphthaline-sulphonates. The esters of formula (I) are prepared by reaction of 7-ACA with bromophtalide or chloromethylpivalate in the presence of an alkylamine, in a solvent selected from the group consisting of dimethylformamide, dimethyl sulphoxide, dimethylacetamide, formamide, at a temperature in the range of 0°–70° C., to provide an ester of 7-ACA, which is reacted in a chlorinated aprotic polar organic solvent and in the presence of an acceptor for hydrochloric acid with chlorohydrate chloride of 4-piridyl-thioacetic acid, the compound of formula (I) being isolated from the reaction mixture as a salt, after washings with acidic water at pH 1–4 and addition of a pharmaceutically acceptable acid, by treatment with a solvent selected from the group consisting of ethyl ether, petroleum ether and hexane.

The compounds of formula (I) may also be prepared by reaction of a cephapirine salt with bromophtalide or chloromethylpivalate in a solvent selected from the group consisting of dimethylformamide, dimethyl sulphoxide, dimethylacetamide and formamide, at a temperature in the range of 0°–70° C., to provide a cephapirine ester, which is isolated as a base by solvent vacuum evaporation at a low temperature, or as a salt thereof by salification with a pharmaceutically acceptable acid, such as hydrochloric acid, p-toluensulphonic acid, β-naphthalen-sulphonic acid.

The compounds of formula (I) and salts thereof are antibiotics having a similar activity as that of cephapirine.

Cephapirine is a compound having the formula

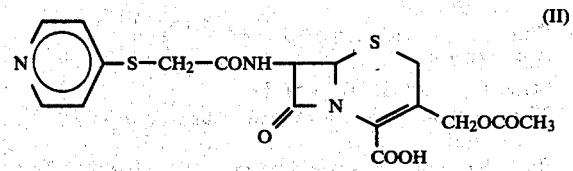

which is per se well known, described in U.S. Pat. No. 3,422,100 and Japanese Pat. No. S 44-26107.

The compounds of formula (I) and salts thereof, as used in oral therapy of bacterial infections, are absorbed in the organism by hydrolization to provide cephapirine.

In order that the characteristics of the present invention be more clearly understood, some unrestrictive exemplary embodiments thereof will now be described.

EXAMPLE 1

Phtalidic Ester Chlorohydrate of 7-ACA

In a flask, 250 ml dimethylformamide (DMF) and 27.2 g (0.1 mole) 7-ACA were charged. The suspension thus obtained at 20° C. was added with 21.93 g (0.103 mole) 3-bromophtalide. The mixture was heated to 40° C. and 10.4 g (0.103 mole) triethylamine (TEA) were dropwise added in 3 hours. After dropwise addition of TEA, the mixture was stirred at 40° C. for further 2 hours. After cooling at 10° C., the mixture was diluted with 300 ml ice water. The pH was adjusted at 1.5 with 37% HCl, then twice extracting with 100 ml methyl isobutylketone (MIBK). The aqueous phase containing phtalidic ester of 7-ACA was added with 100 g NaCl and 300 ml methylene chloride.

The phases were separated, the aqueous phase was extracted again with 150 ml methylene chloride; the combined methylene steps were dried on $MgSO_4$ and the filtrate vacuum evaporated. The residual oil treated with petroleum ether/crystalized as a white solid, which was filtered, washed with petroleum ether and vacuum dried at 40° C. 36 g phtalidic ester chlorohydrate of 7-ACA were obtained.

mp=195°–200° C.

Chlorine titre=7.94% (96% on theoretical).
K.F.=0.5%

$[\alpha]_D$(c=1, methanol): +55°

TLC: single spot (eluent acetonitrile/formic acid=20:1). By following the same process, by using dimethyl sulphoxide (DMSO) instead of dimethylformamide, analogous results were obtained.

EXAMPLE 2

Phtalidic Ester Chlorohydrate of Cephapirine (Phtalpirine Chlorohydrate)

22 g (0.05 mole) phtalidic ester chlorohydrate of 7-ACA were dissolved in 300 ml methylene chloride and at 15° C. 5.05 g (0.05 mole) TEA were added to remove the hydrochloric acid of the chlorohydrate. Then, 30 ml propylene oxide were added, followed by the addition at 15° C. of 11.2 g chlorohydrate chloride of 4-piridyl-thioacetic acid. The mixture was heated to 25° C. and the reaction was allowed for 1.5 hours. The reaction mixture was filtered on dicalite. The methylene solution thus obtained was stratified with 100 ml acidic water (pH 1.5 ) for hydrochloric acid, then separated, and the organic phase dried on sodium sulphate was percolated in 30 minutes in 1000 ml ethyl ether under stirring.

A precipitate was obtained, which after 30 minutes was filtered, washed with ether, then vacuum dried at 40° C. 26.57 g phtalpirine chlorohydrate were obtained.

TLC=single spot (eluent $CH_3CN/HCOOH=20:1$)
K.F.=1.2%
$[\alpha]_D$=(c=1, methanol): +125°
$E_1{}_{cm}^{1\%}$ 260 mμ=252

By repeating the same example, but using bases of acetamide or sodium bicarbonate type as acceptors for hydrochloric acid, analogous results were obtained both as to yield in finished product and quality.

EXAMPLE 3

Tosilate Ester Phtalidic Cephapirine (Phtalpirine Tosilate)

In a flask, 450 ml dimethylformamide were charged, followed by 44.5 g (0.1 mole) sodium salt cephapirine. At 15° C., 21.3 g (0.1 mole) 3-bromophtalide were added, the mixture was heated to 40° C. and the reaction was completed after 1.5 hours. The product was controlled on thin layer chromatography using as eluent $CH_3CN/HCOOH$ 20:1. Upon synthesis completion, the mixture was cooled to 0° C. and diluted with 600 ml ice water, then adding also 300 ml methylene chloride and 19.0 g (0.1 mole) paratoluensulphonic acid monohydrate; pH was adjusted to 1.5–1.7 with 37% hydrochloric acid and after stirring fro 30 minutes the phases were separated. The methylene solution containing phtalpirine tosilate was dried on sodium sulphate, filtered and diluted with 1 l ethyl ether.

The product was crystalized, filtered, washed with 100 ml ether, and vacuum dried at 40° C.

65.3 g phtalpirine tosilate were obtained.
K.F. 1.3%
TLC=single spot
$[\alpha]_D=(c=1,$ methanol$): +105°$
m.p.$=185°$ C.
$E_1 {}_{cm}{}^{1\%}$ 260 m$\mu$=212
Microbiological titre=600 mcg/mg with respect to sodium cephapirine.

By following the same process as above described, but using dimethyl sulphoxide instead of dimethylformamide, analogous results are obtained.

EXAMPLE 4

Naphthalin Sulphonate Ester Phtalidic Cephapirine (Phtalpirine Napsilate)

In a flask, 450 ml DMF were charged, followed by 44.5 g (0.1 mole) cephapirine sodium salt; at 15° C., 21.3 g (0.1 mole) bromophtalide were added, then heating to 35° C. and the reaction was completed after 2 hours. The mixture was cooled to 0° C. and diluted with 600 ml ice water, 300 ml $CH_2Cl_2$ were added, pH was adjusted to 1.3–1.5 with conc. HCl, and 24 g (0.1 mole) naphthalin sodium sulphonate were added, while pH was maintained at 1.3–1.5 with conc. HCl for 30 minutes.

The phases were separated and the methylene phase was dried with anhydrous $Na_2SO_4$, then filtering and diluting with 1,500 ml ethyl ether, obtaining a crystalline product which was filtered, washed with 150 ml ethyl ether and vacuum dried at 40° C.

67 g phtalpirine napsilate were obtained.
K.F.=0.8%
$[\alpha]_D=(c=1,$ methanol$): +100°$
TLC=single spot
$E_1 {}_{cm}{}^{1\%}=260$ m$\mu$=205
Microbiological titre=585 mcg/mr with respect to sodium cephapirine.

By following the same process, as above described, but using dimethyl sulphoxide instead of DMF, analogous results were obtained.

Moreover, if 42.3 g (0.1 mole) acidic cephapirine salified with carboxyl with 10.1 g (0.1 mole) TEA are used instead of sodium cephapirine, the same results as shown in Examples 3 and 4 were obtained.

EXAMPLE 5

Phtalidic Ester of Cephapirine (Phtalpirine)

In a flask, 400 ml DMSO were charged, followed by 44.5 g (0.1 mole) sodium salt cephapirine. At 15° C., 21.3 g (0.1 mole) 3-bromophthalide were added, then heating to 40° C., and the reaction was completed after 1.5 hours, then controlling on thin layer chromatography using $CH_3CN/HCOOH$ 20:1 as eluent.

Upon synthesis completion, the product was cooled to 0° C. and diluted with 550 ml ice water, then adding 37% HCl to pH 1.0–1.2 and extracting twice with 100 ml toluene. The aqueous phase thus obtained was stratified with 300 ml methylene chloride and pH was adjusted to 4.5–5.0 with 4 N NaOH.

The phases were separated and the aqueous phase was extracted again with 50 ml methylene chloride; the extracts were gathered and combined and vacuum evaporated at 10° C. A thick residue was obtained which was crumbled with petroleum ether and filtered.

44 g phtalidic ester of cephapirine were obtained.
K.F.=1%
TLC=single spot
m.p.=135° C. with decomposition
$[\alpha]_D=(c=1,$ methanol$) +136°$
Microbiological titre=750 mcg/mg with respect to acidic cephapirine.

EXAMPLE 6

Pivalic Ester Chlorohydrate of 7-ACA

A flask was charged with 250 ml DMF and 27.2 g (0.1 mole) 7-ACA. At 15° C., 15 g (0.1 mole) chloromethyl pivalate were added, the mixture was heated to 40° C., then adding 1.0 g (0.1 mole) triethylamine in 3 hours and 10 minutes.

At the end of the addition, the mixture was allowed to rest at 40° C. for 2 hours, then cooling to 10° C. and filtering the suspension. The isolated precipitate in addition to triethylchloridrate also contains 7-ACA in an amount of 20% on that initially used, and which was recovered. The filtered solution was cooled to 0° C. and diluted with 100 ml MIBK and 300 ml ice water, pH was adjusted to 0.8 with 37% HCl and after stirring for 10 minutes the solution was decanted. MIBK solution was discarded, while the aqueous phase was added with 50 g sodium chloride and 250 ml methylene chloride. The phases were again separated and the aqueous layer was again extracted with 100 ml methylene chloride. The combined methylene extracts were dried on anhydrous sodium sulphate and the filtrate vacuum evaporated. The residual oil treated with 200 ml petroleum ether crystallized as cream colour solid, which was filtered, washed with petroleum ether and vacuum dried at 40° C.

28.7 g pivalic ester chlorohydrate of 7-ACA were obtained.
m.p.=180°–185° C.
Chlorine $Cl^-$ titre=8.15%, or 97% of theoretical
K.F.=0.35%
$[\alpha]_D(c=1,$ methanol$): +56.5°$
TLC=single spot (eluent acetonitrile/formic acid=20:1)

By following the same process, but using DMSO instead of DMF, analogous results were obtained.

EXAMPLE 7

Cephapirine Pivalic Ester Chlorohydrate (Pivpirine Chlorohydrate)

A reaction flask was charged with 200 ml methylene chloride and 21.13 g (0.05 mole) pivalic ester chlorohydrate of 7-ACA. At 15° C., 5.05 g (0.05 mole) triethylamine were added to remove the hydrochloric acid of the chlorohydrate. After addition of 25 ml propylene oxide and 11.2 g (0.05 mole) chloride chlorohydrate of 4-piridyl-thioacetic acid, the mixture was heated to 25° C. and allowed to react for 1¾ hours. The reaction mixture was filtered on dicalite. The methylene solution thus obtained was stratified with 100 ml acidic water (pH 1.5) for hydrochloric acid, then separated, dried on magnesium sulphate and after filtering diluted under stirring for 30 minutes with 1000 ml ethyl ether.

The precipitate thus formed was filtered after 30 minutes, washed with ether and then vacuum dried at 40° C.

21.5 g cephapirine pivalic ester chlorohydrate (pivpirine chlorohydrate) were obtained.

TLC=single spot (eluent acetonitrile/formic acid=20:1)

K.F.=1%

$[\alpha]_D$(c=1, methanol): +130°

Chlorine Cl− titre=5.87% or 95% of theoretical

Microbiological titre=720 mcg/mg with respect to acidic cephapirine

By repeating the same example, but using different acceptors for hydrochloric acid, such as sodium carbonate and acetamide, analogous results were obtained as to yield and quality of finished product.

EXAMPLE 8

Cephapirine Pivalic Ester Chlorohydrate (Pivpirine Chlorohydrate)

A flask was charged with 290 ml DMF and 22.25 g (0.05 mole) sodium cephapirine, and at 15° C. added with 7.52 g (0.05 mole) chloromethyl pivalate. The temperature was risen to 35° C. and stirring was continued for 12 hours. After 12 hours the reaction was completed, the mixture cooled to 0° C., diluted with 300 ml water saturated with sodium chloride, pH was adjusted to 1.0–1.2 with 37% hydrochloric acid and after stirring for 15 minutes the phases were decanted. The aqueous phase was again extracted with 100 ml methylene chloride. The combined methylene extracts were dried on magnesium sulphate and the filtrate was added in 30 minutes to 2000 ml ethyl ether. The precipitate thus formed was filtered, washed with ethyl ether and vacuum dried at 40° C.

22.5 g cephapirine pivalic ester chlorohydrate (pivpirine chlorohydrate) were obtained.

K.F.=1.3%

TLC=single spot (eluent acetonitrile/formic acid=20:1)

$[\alpha]_D$(c=1, methanol): +132°

Chlorine titre=5.93% or 96% of theoretical $E_{1\ cm}^{1\%}$ 260 m$\mu$=270

Microbiological titre=721 mcg/mg as acidic cephapirine

By following the same process as above described, but using DMSO instead of DMF, analogous results were obtained.

EXAMPLE 9

Cephapirine Pivalic Ester Tosilate (Pivpirine Tosilate)

A reaction flask was charged with 200 ml methylene chloride and 21.13 g (0.05 mole) pivalic ester chlorohydrate of 7-ACA. At 0° C., 5.05 g (0.05 mole) were added to remove the hydrochloric acid of the chlorohydrate. Then, 3.54 g (0.06 mole) acetamide and 11.2 g of chloride chlorohydrate of 4-piridyl-thioacetic acid were added. The temperature was risen to +5° C. and the mixture was maintained at this temperature under stirring for 1.5 hours. The reaction mixture thus obtained was filtered on dicalite, then adding 100 ml water saturated with sodium chloride, 9.5 g paratoluenesulphonic acid monohydrate (0.05 mole) and hydrochloric acid to pH 1.0–1.2. After stirring for 30 minutes at this pH, the mixture was decanted at 10° C. and the organic phase dried on anhydrous $Na_2SO_4$, then adding in 30 minutes to 1,500 ml ethyl ether. The precipitate thus formed was filtered after 30 minutes, washed with ether and vacuum dried at 40° C.

26.55 g cephapirine pivalic ester tosilate (pivpirine tosilate) were obtained.

K.F.=2.2%

TLC=single spot (eluent acetonitrile/formic acid=20:1)

$[\alpha]_D$(c=1, methanol): +108°

$E_{1\ cm}^{1\%}$ 260 m$\mu$=220

Microbiological titre=575 mcg/mg on acidic cephapirine.

m.p.=191°–195° C.

By following the above described example, various salts of pivpirine may be obtained by using (0.05 mole) of an acid such as, for example, of the β-naphthalin-sulphonic type, obtaining the respective napsilates.

EXAMPLE 10

Cephapirine Pivalic Ester (Pivpirine)

A reaction flask was charged with 200 ml DMSO and 22.25 g (0.1 mole) sodium salt cephapirine. At 15° C., 7.52 g 0.05 mole) chloromethylpivalate were added. The temperature was risen to 40° C. and the reaction was completed after 12 hours.

Upon synthesis completion, the mixture was cooled to 0° C. and diluted with 200 ml ice water, 37% HCl was added to pH 1.0–1.2, the extracting twice with 50 ml toluene. The aqueous phase thus obtained was stratified with 150 ml methylene chloride and brought to pH 4.5–5.0 with 4 N NaOH.

The phases were separated and the aqueous phase was extracted again with 30 ml methylene chloride. The methylene extracts were combined and vacuum evaporated at 10° C.

A thick residue was obtained and crumbled with petroleum ether, filtered and washed with 30 ml petroleum ether, thus obtaining 42 g cephapirine pivalic ester (pivpirine).

K.F.=0.7%

TLC=single spot m.p.=115° C. (decomposition)

$[\alpha]_D$=(c=1, methanol): +140°

Microbiological titre: 770 mcg/mg on acidic cephapirine.

What we claim is:

1. Cephapirine esters having the formula

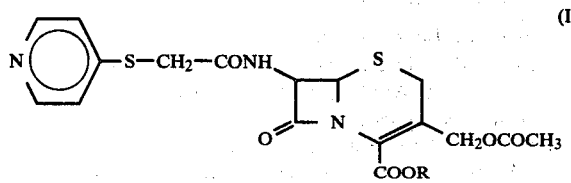 (I)
wherein R is
—CH$_2$OCOC(CH$_3$)$_3$.
2. Pharmaceutically acceptable salts of the esters of formula (I) of claim 1.
3. Pharmaceutically acceptable salts of the esters of formula (I) of claim 1, selected from the group consisting of chlorohydrates, p-toluen sulphonates and β-naphthalin-sulphonates of such esters.
* * * * *